United States Patent
Terike et al.

(10) Patent No.: US 10,705,162 B2
(45) Date of Patent: Jul. 7, 2020

(54) TEMPERATURE CONTROLLED MAGNETIC PERMEABILITY DETECTOR

(71) Applicant: LIFEASSAYS AB, Lund (SE)

(72) Inventors: Khaled Terike, Helsingborg (SE); Filiz Ibraimi, Malmö (SE)

(73) Assignee: LIFEASSAYS AB, Lund (SE)

( * ) Notice: Subject to any disclaimer, the term of this patent is extended or adjusted under 35 U.S.C. 154(b) by 0 days.

(21) Appl. No.: 15/777,311

(22) PCT Filed: Dec. 1, 2016

(86) PCT No.: PCT/SE2016/051200
§ 371 (c)(1),
(2) Date: May 18, 2018

(87) PCT Pub. No.: WO2017/095317
PCT Pub. Date: Jun. 8, 2017

(65) Prior Publication Data
US 2018/0348312 A1    Dec. 6, 2018

(30) Foreign Application Priority Data
Dec. 3, 2015  (SE) ...................................... 1551589

(51) Int. Cl.
*G01N 27/72* (2006.01)
*G01R 33/12* (2006.01)
(Continued)

(52) U.S. Cl.
CPC .......... *G01R 33/1223* (2013.01); *G01N 1/00* (2013.01); *G01N 27/02* (2013.01); *G01N 27/72* (2013.01);
(Continued)

(58) Field of Classification Search
CPC .... B29C 66/71; B29C 66/7212; G01N 27/72; G01N 27/9033; G01N 27/9046; G01R 33/028; G01R 33/12; G01R 33/1223
(Continued)

(56) References Cited

U.S. PATENT DOCUMENTS 5,793,199 A   8/1998  Kasahara et al.
6,110,660 A   8/2000  Kriz et al.
(Continued)

FOREIGN PATENT DOCUMENTS

FR    2486661 A1   1/1982
GB    1215293      12/1970
(Continued)

OTHER PUBLICATIONS

FR 2486661 Machine Translation, Jan. 15, 1982. (Year: 1982).*
(Continued)

*Primary Examiner* — Raul J Rios Russo
(74) *Attorney, Agent, or Firm* — Leason Ellis LLP

(57) ABSTRACT

A device for detection of magnetic permeability ($\mu$) or, alternatively, relative magnetic permeability ($\mu r$) or, alternatively relative magnetic susceptibility ($\mu r$-) of a sample is described. The device comprises a sample chamber having at least one opening for introduction of a sample or a sample container holding a sample and an electronic circuit. The device also comprises a coil surrounding said sample chamber, and also an electronic circuit adapted to measure the inductance of said coil. The sample chamber, coil and at least one component of the electronic circuit are placed in a temperature controlled zone. Said at least one component in said electronic circuit is/are selected from the group consisting of capacitors, sensors, precision voltage references, precision regulators, low pass and or high pass filters.

8 Claims, 4 Drawing Sheets

Electronic circuit for measurement of magnetic permeability, subjected to a temperature controlled action

(51) Int. Cl.
| | |
|---|---|
| *G01N 27/76* | (2006.01) |
| *G01N 1/00* | (2006.01) |
| *G01N 33/483* | (2006.01) |
| *G01R 33/16* | (2006.01) |
| *G01N 27/02* | (2006.01) |
| *G01N 27/90* | (2006.01) |
| *G01R 33/028* | (2006.01) |
| *B29C 65/00* | (2006.01) |

(52) U.S. Cl.
CPC ......... *G01N 27/76* (2013.01); *G01N 27/9033* (2013.01); *G01N 27/9046* (2013.01); *G01N 33/483* (2013.01); *G01R 33/028* (2013.01); *G01R 33/12* (2013.01); *G01R 33/16* (2013.01); *B29C 66/71* (2013.01); *B29C 66/7212* (2013.01)

(58) Field of Classification Search
USPC ... 324/51, 55, 200, 219, 228, 233, 239, 254, 324/257, 260
See application file for complete search history.

(56) References Cited

U.S. PATENT DOCUMENTS

| | | | |
|---|---|---|---|
| 6,995,021 B2 | 2/2006 | Laitinen et al. | |
| 2005/0093535 A1* | 5/2005 | Kriz | G01N 27/72 324/201 |
| 2011/0104659 A1* | 5/2011 | Kriz | G01R 33/1223 435/5 |
| 2015/0217262 A1* | 8/2015 | Wagner | A61K 49/06 424/9.3 |
| 2015/0338376 A1* | 11/2015 | Waanders | G01R 33/0017 324/201 |
| 2016/0178710 A1* | 6/2016 | Fidler | G01R 33/1223 324/239 |

FOREIGN PATENT DOCUMENTS

| | | |
|---|---|---|
| WO | 9319381 A1 | 9/1993 |
| WO | 03076931 A1 | 9/2003 |

OTHER PUBLICATIONS

Ibraimi et al. "Preparation of a portable point-of-care in 1-9 vito diagnostic system, for quantification of canine C-reactive protein, based on a magnetic two-site immunoassay." Analytical and Bioanalytical Chemistry Jul. 2013, vol. 405, Issue 18, pp. 6001-6007.

International Search Report for International Patent Application No. PCT/SE2016/0501200 dated Mar. 15, 2017. 5 pages.

Kriz, Kirstin, et al. "Detection of C-reactive protein utilizing magnetic permeability detection based immunoassays." Analytical chemistry 77.18 (2005): 5920-5924.

European Search Report in corresponding EP Application No. 16871158.8, dated Apr. 8, 2019.

* cited by examiner

Circuit for measurement of magnetic permeability, not subjected to a temperature controlled action Electronic circuit for measurement of magnetic permeability, subjected to a temperature controlled action

TEMPERATURE CONTROLLED MAGNETIC PERMEABILITY DETECTOR

CROSS-REFERENCE TO RELATED APPLICATIONS

This application is a U.S. National Stage application under 35 U.S.C. § 371 of International Patent Application No. PCT/SE2016/051200, which was filed on Dec. 1, 2016, which claims priority to Swedish Patent Application No. SE 1551589-3, which was filed on Dec. 3, 2015, both of which are hereby incorporated by reference in their respective entireties.

FIELD OF THE INVENTION

The present invention relates to a device for detection of magnetic permeability ($\mu$) or, alternatively, relative magnetic permeability ($\mu r$) or, alternatively relative magnetic susceptibility ($\mu r$-1) of a sample, said device comprising a sample chamber having at least one opening for introduction of a sample or a sample container holding a sample, said device also comprising a coil surrounding said sample chamber, and also comprising an electronic circuit adapted to measure the inductance of said coil, wherein said sample chamber, said coil and at least one component of said electronic circuit are placed in a temperature controlled zone and wherein said at least one component in said electronic circuit is/are selected from the group consisting of capacitors, sensors, precision voltage references, precision regulators, low pass and or high pass filters.

The present invention also relates to use of a device according to the invention.

BACKGROUND ART

The annual world market for diagnostic equipment based on immunoassays has increased considerably in the last decades. The main reason for the success of immunoassays is that it is easy to adjust to various chemical analysis problems. By using different types of detection techniques in combination with immunoassays, a number of important chemical substances can be identified and quantified. Depending on the physical measuring principle, different types of detectors are suitable for different types of analysis problems. Since the introduction of immunoassays, many new detectors have been presented.

A number of magnetic technologies have been incorporated into devices for different quantitative measurement purposes. Examples of the technologies are magnetic permeability ($\mu$), relative magnetic permeability ($\mu r$) and relative magnetic susceptibility ($\mu r$-1).

The temperature dependency of magnetic permeability ($\mu$), relative magnetic permeability ($\mu r$) and relative magnetic susceptibility ($\mu r$-1) has been taken into account earlier when constructing devices bases on these technologies. In F. Ibraimi et al, Anal Bioanal Chem DOI 10.1007/s00216-013-7032-9, 1-7, 2013, an inductance coil for measurement of magnetic permeability maintained at a constant temperature (30° C.) is described.

U.S. Pat. No. 6,700,389 describes a device and a method wherein the temperature of an inductive coil is determined to adjust the inductance measured.

U.S. Pat. No. 7,910,063 describes a further approach to compensate for the changes in coil temperature. According to this document, a device and a process for measurement of magnetic permeability is described. Samples are placed in a measuring coil measuring the inductance of the sample, which thereafter is compared and compensated with a well-known reference signal achieved by measurements at the same temperature conditions. This type of device allows measurements of the magnetic permeability for samples, but suffers from the drawback that two coils have to be used in the device.

All the above mentioned techniques further suffer from the drawback that the temperature-dependent drift of electrical components (other than the inductance coil) present in the electrical circuit limits the sensitivity (signal to noise ratio) of the detector.

SUMMARY OF THE INVENTION

The aim of the present invention is thus to solve the problems mentioned above with temperature-dependent drift.

According to the present invention this is done by providing a device for detection of magnetic permeability ($\mu$) or, alternatively, relative magnetic permeability ($\mu r$) or, alternatively relative magnetic susceptibility ($\mu r$-1) of a sample, said device comprising a sample chamber having at least one opening for introduction of a sample or a sample container holding a sample, said device also comprising a coil surrounding said sample chamber, and also comprising an electronic circuit adapted to measure the inductance of said coil, wherein said sample chamber, said coil and at least one component in said electronic circuit are placed in a temperature controlled zone and wherein said at least one component in said electronic circuit is/are selected from the group consisting of capacitors, sensors, precision voltage references, precision regulators, low pass and or high pass filters.

According to another embodiment, all capacitors, sensors, precision voltage references, precision regulators, low pass and or high pass filters of the electronic circuit are placed in the temperature controlled zone.

In one embodiment of the present invention said coil, when filled with air, has an inductance in the range of 0.01 to 100 pH.

According to a further embodiment, said sample chamber has a chamber volume of 0.1 to 5000 µl.

In one embodiment, said sample chamber is made of a polymer, wood, glass, or a metal with $0.999<\mu r<1.001$.

In a further embodiment, the polymer is chosen from the group consisting of polyoxymethylene, polyvinyl chloride, Teflon®, polyamide, polyacetal, polyethylene, polycarbonate, polystyrene, or polypropylene.

The present invention further relates to use of a device according to the above for detection of chemical substances.

According to one embodiment the chemical substance has a $\mu r=1$.

In one embodiment the chemical substance is chosen from the group consisting of proteins, hormones, complement factors, bacteria, cells, viruses, fungi, yeast, spores, phages, cell organelles, DNA and RNA.

The right side circuit shows a temperature control circuit, which circuit controls the temperature of the coil L2 of the left side circuit, keeping the temperature at the given set point temperature. By this temperature control, the output of the differential amplifier 104 is not affected by any temperature variation of the coil L2, thus giving a more sensitive and accurate result.

Figure 1:
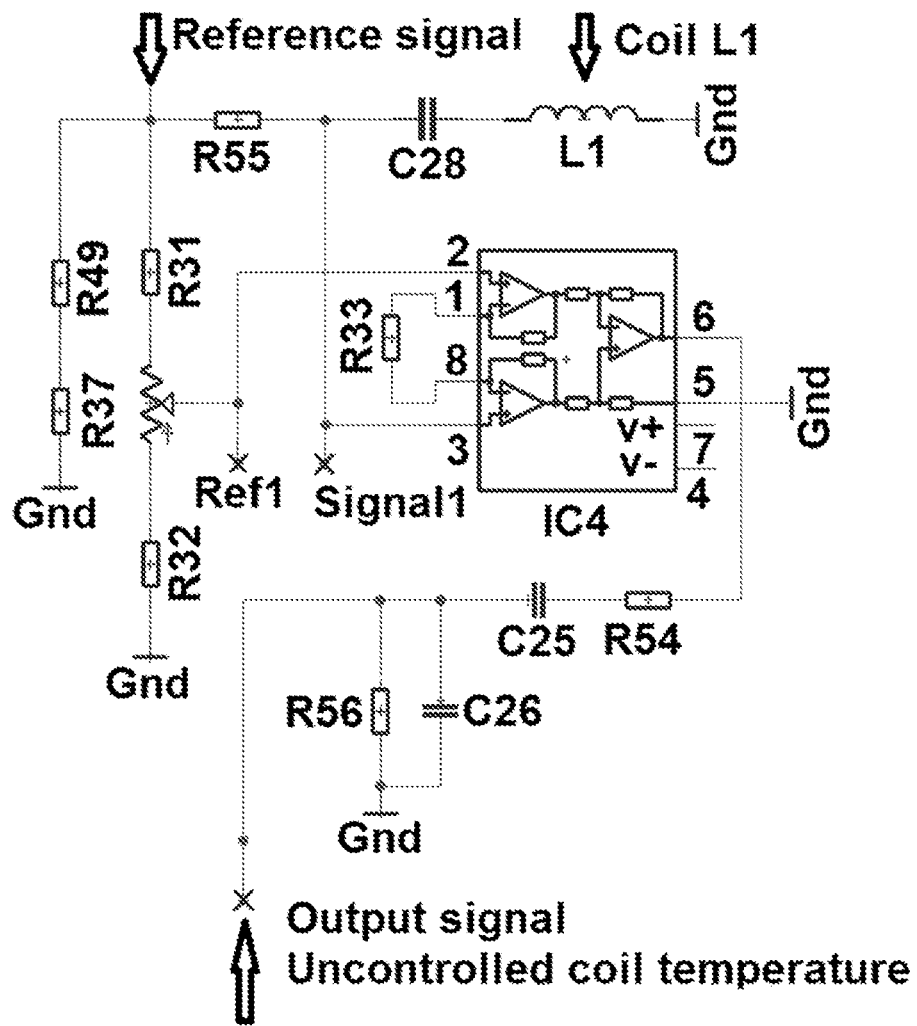
FIG. 1 is a basic diagram showing an example of an electronic circuit for measurement of magnetic permeability, wherein no temperature controlled zone is present.
Figure 2:
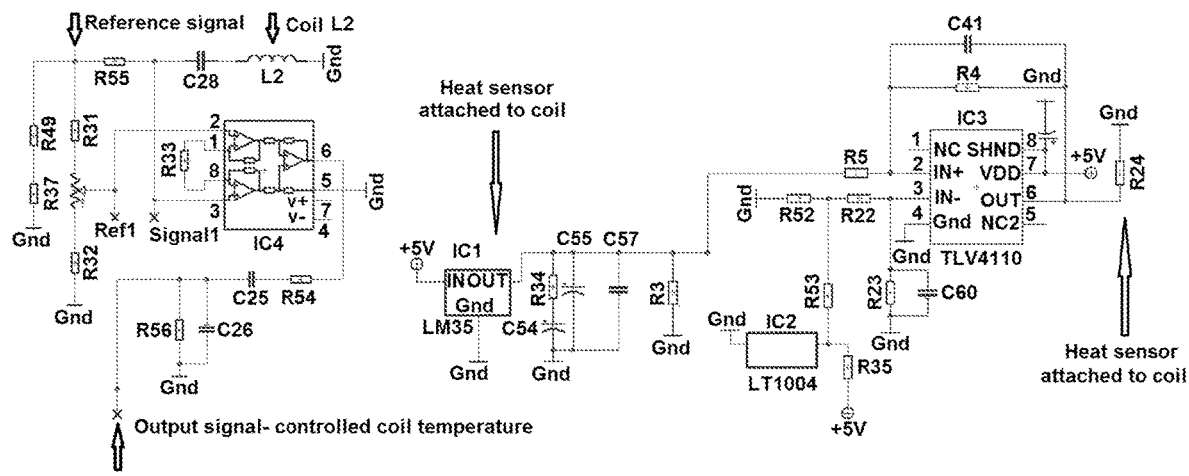
FIG. 2 is a basic diagram showing an example of an electronic circuit for measurement of magnetic permeability, wherein the electronic circuit is subject to a temperature controlled zone.
Figure 3:
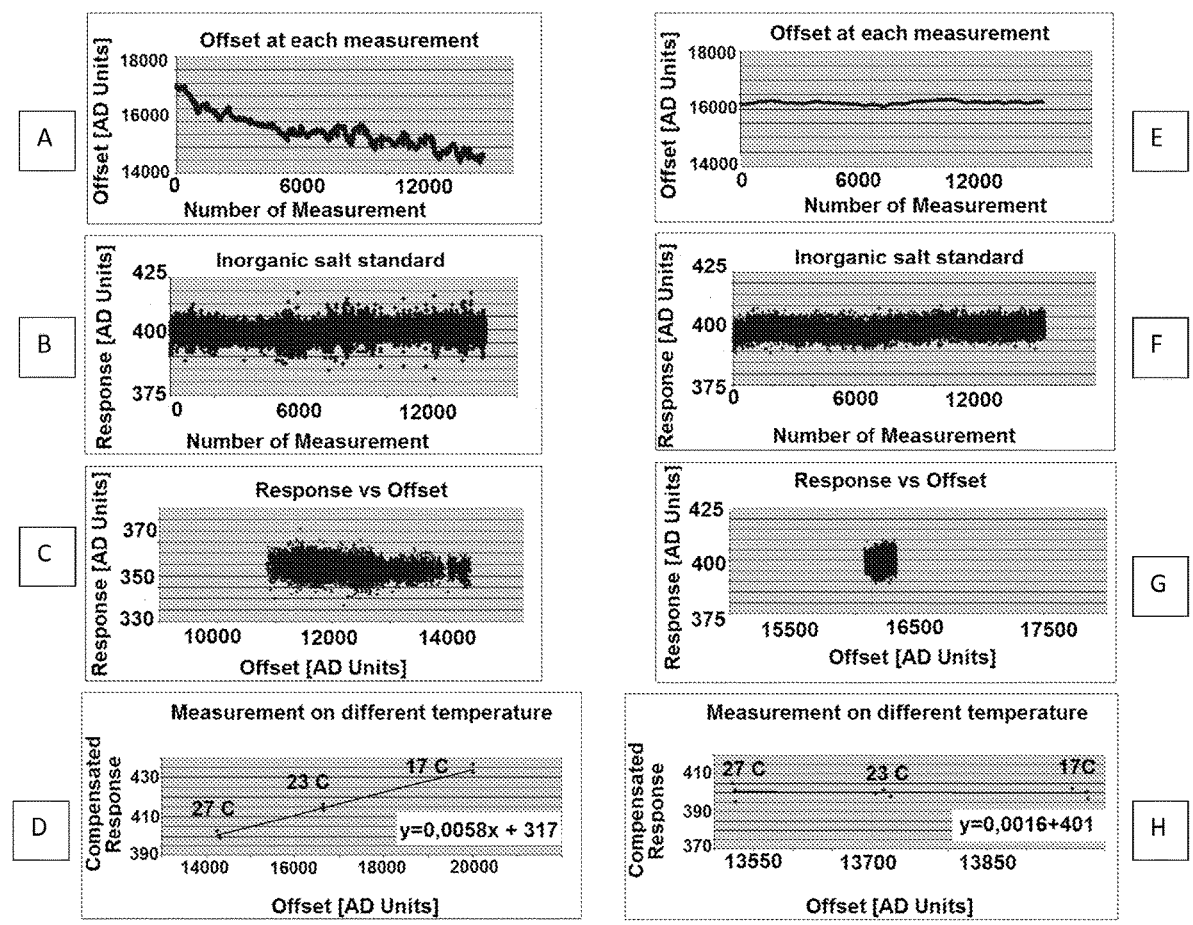

FIG. 3 shows diagrams showing the characteristics of the measurements of a device for quantification of magnetic permeability, wherein the electronic circuit is not subject to a temperature controlled zone (left column), and also showing the characteristics of the measurements of a device according to the present invention wherein the electronic circuit is subject to a temperature controlled zone (right column).

Figure 4:
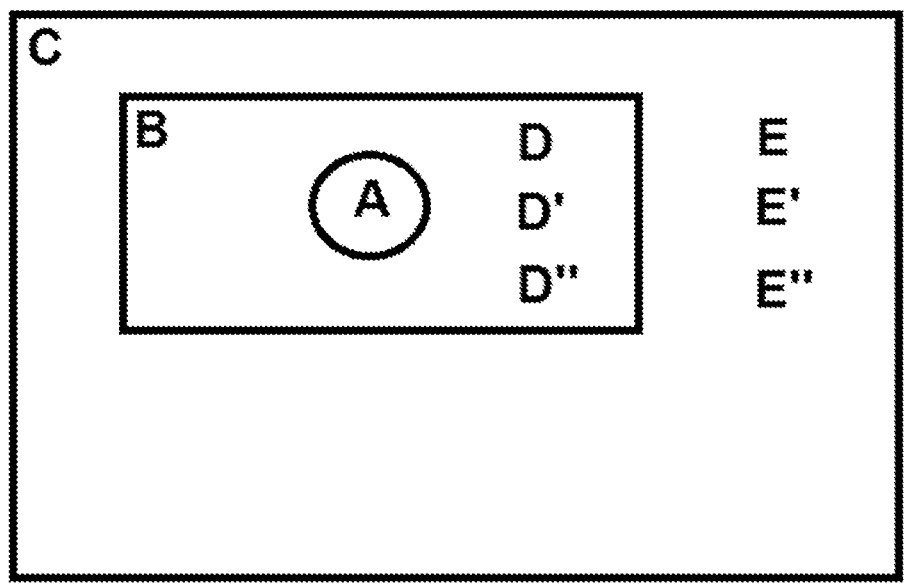

FIG. 4 shows schematically a device according to the present invention, where A is a coil, B is a temperature controlled zone of the electronic circuit, C is a non temperature controlled zone of the electronic circuit, D, D', D" are electronic components in a temperature controlled zone, and E, E', E" are electronic components in a non temperature controlled zone.

DETAILED DESCRIPTION OF THE INVENTION

As stated above, the present invention relates to a device for detection of magnetic permeability ($\mu$) or, alternatively, relative magnetic permeability ($\mu r$) or, alternatively relative magnetic susceptibility ($\mu r$-1) of a sample, said device comprising a sample chamber having at least one opening for introduction of a sample or a sample container holding a sample, said device also comprising a coil surrounding said sample chamber, and also comprising an electronic circuit adapted to measure the inductance of said coil, wherein said sample chamber, said coil and at least one component in said electronic circuit are placed in a temperature controlled zone and wherein said at least one component in said electronic circuit is/are selected from the group consisting of capacitors, sensors, precision voltage references, precision regulators, low pass and or high pass filters.

Not all types of electronic components may be placed in a temperature controlled zone. Coils, capacitors, sensors, precision voltage references, precision regulators, low pass and high pass filters are suitable for placing in a temperature controlled zone, while for instance A/D converters are disturbed by the current, and therefore should be placed further away from analogous signals.

When power is applied to the device according to the present invention a voltage reference IC2 has the same temperature as a set point temperature given to the coil L2. The heat sensor IC1 has the actual temperature of the coil. This forces the output of IC3 to be at its highest voltage level as long as the difference between the set point temperature and the actual temperature value is above zero. As the heat resister warms the coil L2, the difference between the set point temperature and the actual temperature decreases until the actual temperature reaches the set point temperature, where no more heat needs to be provided until the actual temperature decreases, and there is a difference between the set point temperature and the actual temperature again.

The coil L2 is preferably coated with an aluminum coating, to which the sensor IC1 and the heat resister R24, are attached.

The sensor IC1 is a precision integrated-circuit temperature sensor which is connected to the aluminum coating of the coil L2. The output voltage of IC1 is linearly proportional to the temperature in degrees Celsius of the coating of the coil L2.

IC2 is a voltage reference circuit, giving the set point temperature of the coating of the coil L2.

IC3 is a circuit that compares the set point temperature (set by IC2) and the output voltage of IC1, thereby deciding if heating of the coating of the coil L2 is necessary or not.

Thus, by providing a temperature control/regulation the output signal will be independent of the variation of the coil temperature and thus more accurate.

In FIG. 3 the left columns show diagrams showing the characteristics of the measurements of a device for quantification of magnetic permeability wherein the electronic circuit is not subject to additional temperature control.

Diagram A shows the long term drift in off-set versus time/number of measurements.

Diagram B shows the imprecision of the measurements of off-set using an inorganic salt aqueous standard.

Diagram C shows the imprecision versus off-set (long term drift in offset).

Diagram D shows the imprecision versus offset at three different temperatures 17° C., 23° C., 27° C.

In FIG. 3, the right columns show the characteristics of the measurements of a device according to the present invention wherein the electronic circuit is subject to an additional temperature control according to the present invention.

Diagram E shows the long term drift in off-set versus time/number of measurements.

Diagram F shows the imprecision of the measurements of off-set using an inorganic salt aqueous standard.

Diagram G shows the shows the imprecision versus off-set (long term drift in off-set).

Diagram H shows the imprecision versus offset in three different temperatures 17° C., 23° C., 27° C.

The device according to the present invention can advantageously be used for detection of chemical substances. Preferably the chemical substances have a $\mu r$=1. The chemical substances to be detected may be chosen from the group consisting of proteins, hormones, complement factors, bacteria, cells, viruses, fungi, yeast, spores, phages, cell organelles, DNA and RNA.

The invention claimed is:

1. A device for detection of magnetic permeability ($\mu$) or, alternatively, relative magnetic permeability ($\mu r$) or, alternatively relative magnetic susceptibility ($\mu r$-1) of a sample, said device comprising a sample chamber having at least one opening for introduction of a sample or a sample container holding a sample, said device also comprising a coil surrounding said sample chamber, and also comprising an electronic circuit adapted to measure the inductance of said coil, wherein said sample chamber, said coil, at least one heat sensor and at least one component in said electronic circuit are placed in a temperature controlled zone, wherein said at least one component in said electronic circuit is/are selected from the group consisting of capacitors, sensors, precision voltage references, precision regulators, low pass and or high pass filters and wherein said coil in the tempersature controlled zone is heated by a heat resistor.

2. The device according to claim 1, wherein all capacitors, sensors, precision voltage references, precision regulators, low pass and or high pass filters of the electronic circuit are placed in the temperature controlled zone.

3. The device according to claim 1, wherein said coil, when filled with air, has an inductance in the range of 0.01 to 100 $\mu$H.

4. The device according to claim 1, wherein said sample chamber has a chamber volume of 0.1 to 5000 µl.

5. The device according to claim 1, wherein said sample chamber is made of a polymer, wood, glass, or a metal with $0.999<\mu r<1.001$.

6. The device according to claim 5, wherein the polymer is chosen from the group consisting of polyoxymethylene, polyvinyl chloride, Teflon®, polyamide, polyacetal, polyethylene, polycarbonate, polystyrene, or polypropylene.

7. The device according claim 1, wherein the device is suitable for detection of chemical substances.

8. The device of claim 7, wherein the chemical substances are selected from the group consisting of proteins, hormones, complement factors, bacteria, cells, viruses, fungi, yeast, spores, phages, cell organelles, DNA and RNA.

* * * * *